United States Patent [19]

Skottun

[11] Patent Number: 5,489,302
[45] Date of Patent: Feb. 6, 1996

[54] ACCOMMODATING INTRAOCULAR LENS

[76] Inventor: Bernt C. Skottun, 273 Mather St., Piedmont, Calif. 94611

[21] Appl. No.: 248,509

[22] Filed: May 24, 1994

[51] Int. Cl.⁶ ........................................... A61F 2/16
[52] U.S. Cl. ................................................... 623/6
[58] Field of Search ............................ 623/4, 5, 6

[56] References Cited

U.S. PATENT DOCUMENTS

| | | | |
|---|---|---|---|
| 4,074,368 | 2/1978 | Levy, Jr. et al. | 623/6 |
| 4,254,509 | 1/1981 | Tennant | 623/6 |
| 4,585,457 | 4/1986 | Kalb | 623/6 |
| 4,704,122 | 11/1987 | Portnoy | 623/6 |
| 4,731,078 | 3/1988 | Stoy et al. | 623/6 |
| 4,790,847 | 12/1988 | Woods | 623/6 |
| 4,932,966 | 6/1990 | Christie et al. | 623/6 |
| 5,275,623 | 1/1994 | Sarfarazi | 623/6 |
| 5,391,202 | 2/1995 | Lipshitz et al. | 623/6 |

OTHER PUBLICATIONS

Thornton, S. P. Lens implantation with restored accommodation Current Canadian Ophthalmic Practice vol. 4 No. 2 Jun. 1986.
Hara, T. et al. Accommodative Intraocular lens with Spring Action Part 1. Ophthalmic Surgery, 1990, vol. 21 No. 2, pp. 128–133.
Hara, T. et al. Accommodative Intraocular lens with Spring Action Part 2. Ophthalmic Surgery, vol. 23, No. 9, pp. 632–635.

*Primary Examiner*—Randy C. Shay

[57] ABSTRACT

An intraocular lens for implantation in the posterior chamber of human eyes. The lens has the ability to change its power in response to tension in the ciliary muscle of the eye. A medium of less refractive power than the surrounding aqueous is contained between two transparent membranes (10). By making at least one of these membranes (10) have a concave shape, a lens with positive power is created. By fashioning at least one of the transparent membranes from a resilient material it is possible to make the lens have the ability to alter its power. Change in lens power is accomplished by manipulating the pressure in the interior of the lens. The pressure can be varied by varying the volume of the lens. By means of haptics which either displace part of the side wall of the lens or change the separation between the front and back surface of the lens in response to changes in tension in the ciliary muscle, the volume can be changed. Since the lens chamber (22) is sealed off from the surrounding medium the change in volume results in a change in pressure. Change in pressure causes the flexible lens membranes to change shape thereby changing lens power.

15 Claims, 9 Drawing Sheets

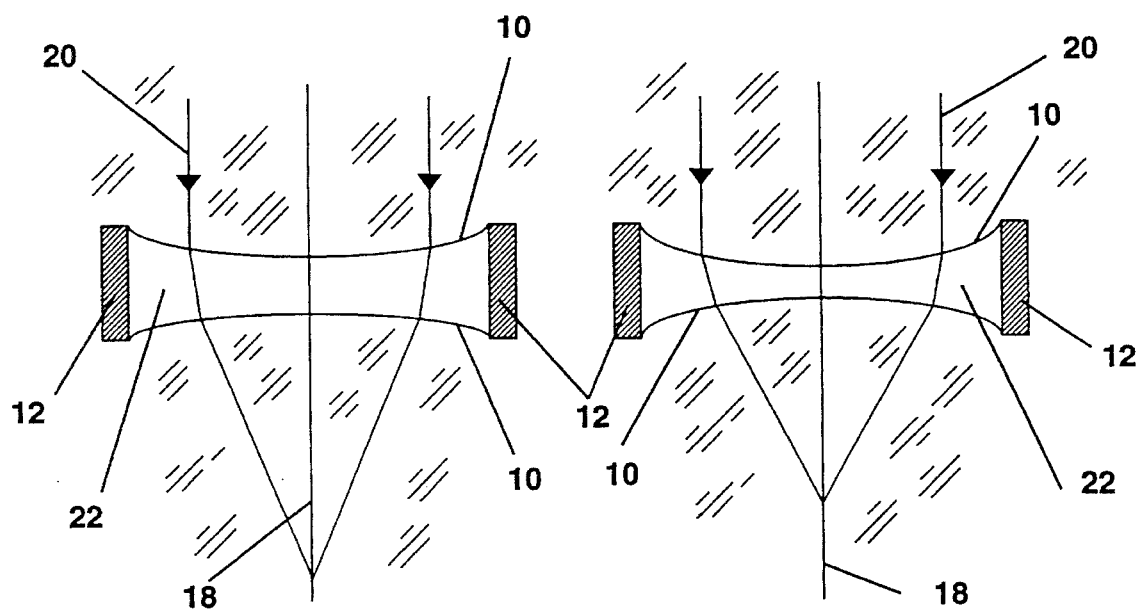
Fig. 1  Fig. 2
Fig. 3
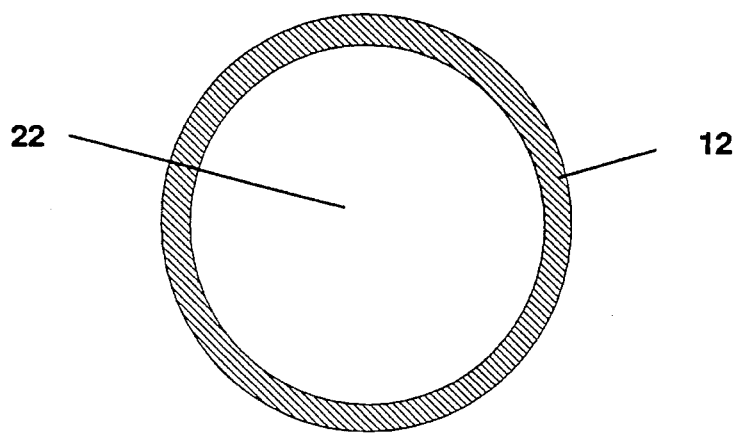

ACCOMMODATING INTRAOCULAR LENS

BACKGROUND-FIELD OF INVENTION

This invention relates to intraocular lenses, specifically to intraocular lenses which have the ability to alter their refractive power in response to changes in the tension of the ciliary muscle of the eye.

BACKGROUND-DESCRIPTION OF PRIOR ART

The first implantation of an artificial lens into a human eye was carried out by Ridley in 1949. Since then several million intraocular lenses have been implanted in the eyes of cataract patients. Today the vast majority of cataract operations involve the implantation of an artificial lens. However, with the exception of a very few experimental lenses these implanted lenses have a fixed focal length or, in the case of bifocal or multifocal lenses, have a few different fixed focal lengths. These lenses therefore lack the ability of the natural lens to change power so as to be able to focus sharply on the retina objects at a continuum of distances from the eye.

Some previous attempts have been made at creating accommodating intraocular lenses. A simple way of varying the effective power of an intraocular lens is by equipping a single fixed power lens with attachments so that it may move back and forth along the optical axis of the eye in response to changes in tension in the ciliary muscle (U.S. Pat. No. 4,254,509 to Tennant 1981; U.S. Pat. No. 4,790,847 to Woods 1988). However, it appears that only a limited amount of change in refractive power can be achieved in this manner (Thornton, 1986).

Hara et al. (1990, 1992) created a system consisting of two lenses held together in a spring arrangement. Accommodation occurs by varying the distance between the lenses. An obvious problem with this system is that it necessarily depends on very fine and fragile springs which could easily be damaged in handling.

Another attempt at creating an accommodating intraocular lens (U.S. Pat. No. 4,932,966 to Christie et al. 1990) has been to use a liquid filled lens to which are attached liquid filled bladders. The bladders and the lumen of the lens are in free communication. The whole assembly is placed inside the empty lens capsule, in such a way that the pressure from the lens capsule is transmitted to the bladders. Increased pressure on the bladders makes liquid move from the bladders to the lumen of the lens, so as to increase the volume (and pressure) of the lens and make it take on a more curved shape. This causes the lens to increase its power. The drawbacks with this approach are that the lens is large and cannot easily be compressed for implantation. Because of its large size it may be difficult to implant and may require large incisions in the cornea. Large corneal incisions are associated with postoperative astigmatism. Also, in order to function properly the lens requires that the lens capsule is left relatively intact, which may be difficult to achieve considering that, due to the large size of the lens, a large incision in the lens capsule is required for placing the lens in the capsule. Furthermore, in order for the lens to work it needs to be filled with a liquid with substantially higher refractive index than that of the surrounding aqueous. While such liquids exist it may turn out to be difficult to find one which will not harm the eye if the lens were to accidentally rupture. For example, filling the lens with oil, as was suggested by Christie et al, may not be safe since the oil may, following accidental rupture, find its way to the anterior chamber and block the angle so as to cause glaucoma. A further difficulty associated with this design is the need to be able to fill the lens with liquid without trapping air in the process.

While most intraocular lenses have a convex shape, concave lenses (U.S. Pat. No. 4,704,122 to Portnoy 1987) or lenses having concave elements (U.S. Pat. No. 4,074,368 to Levy and Pegis 1978) have been proposed. In order to provide positive power these concave elements need to be filled with a substance of refractive index less than that of the surrounding material. Stoy and Stoy (U.S. Pat. No. 4,731,078; 1988) described a variable power lens which incorporates optical materials of low refractive index. However, none of these inventions which have made use of concave elements have incorporated means whereby the tension in the ciliary muscle can dynamically control the power of the lens.

OBJECTS AND ADVANTAGES

Several objects and advantages of the present invention are:

(a) to provide an intraocular lens with the ability to alter its refractive power in response to changes in tension of the ciliary muscle, so as to bring to focus on the retina images of objects over a continuous range of distances, i.e. to accommodate;

(b) to provide an accommodating intraocular lens which is simple in design so as to be easy to manufacture;

(c) to provide an accommodating intraocular lens that is compatible with standard procedures for extracapsular cataract surgery (which may involve capsulectomy of a substantial portion of the anterior capsule);

(d) to provide an accommodating intraocular lens with few moving parts so as to reduce the risk of irritating delicate tissue in the eye thereby reducing the chance of inflammation;

(e) to provide an accommodating intraocular lens which is of light weight so as to put little load on the areas where it makes physical contact with structures of the eye;

(f) to provide an accommodating intraocular lens which is safe, and does not rely on liquids which may be toxic to the tissue of the eye or which may cause glaucoma should these liquids be accidentally released into the interior of the eye;

(g) to provide an accommodating intraocular lens which can be built using materials currently available for use in intraocular implants;

(h) to provide an accommodating intraocular lens which can be implanted using essentially established surgical procedures so as not to require surgeons to undergo substantial re-training;

(i) to provide an accommodating intraocular lens which, for its refractive power, relies on a medium with a refractive index substantially different from that of the surrounding aqueous thereby not requiring very curved refracting surfaces, which in turn allows the lens to occupy only a small volume, i.e. it can be very thin, and has the additional advantage of making it possible to change lens power with only minor changes in lens shape and volume;

(j) to provide an accommodating intraocular lens which is robust and whose various optical parts cannot easily become misaligned.

DRAWING FIGURES

FIG. 1 shows a longitudinal cross section, i.e. a section along the optical axis, through the lens in a condition of low power.

FIG. 2 shows a longitudinal cross section through the lens when it is in a state of high power.

FIG. 3 shows a transverse cross section, i.e., a section perpendicular to the optical axis, through the lens.

Figure 4:
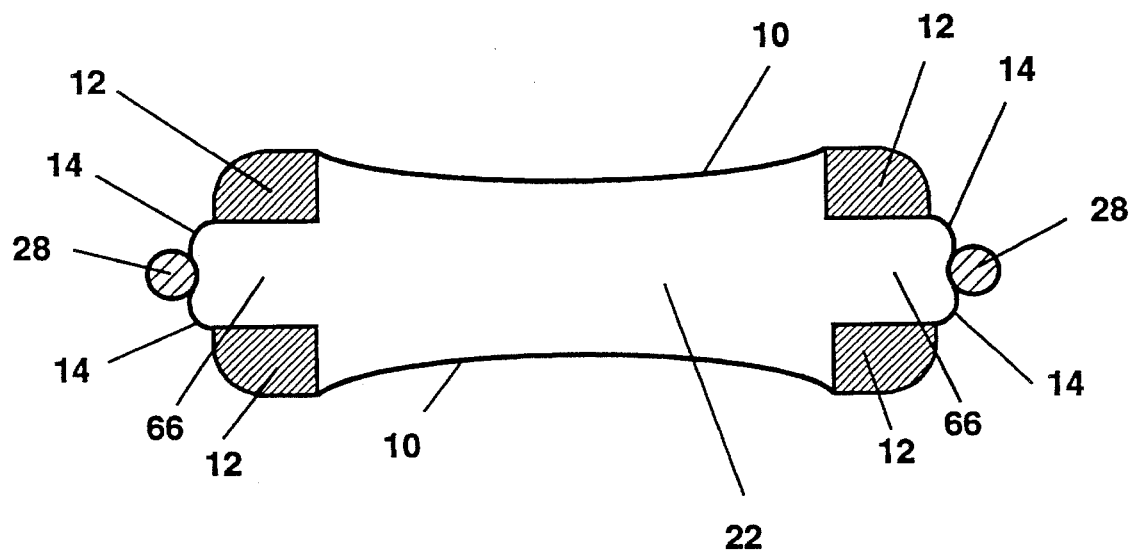
FIG. 4 shows a longitudinal cross section through the lens in order to illustrate the relationship between the cross bars of the haptics and the lens body (the contact sections of the haptics are not shown).

| Reference Numerals In Drawings | |
|---|---|
| 10 transparent membrane | 12 rigid side wall |
| 14 flexible part of side wall | 16 rigid side wall ring |
| 18 optic axis | 20 light ray |
| 22 lens chamber | 24 haptic |
| 26 side bar | 28 cross bar |
| 30 contact section | 32 optic |
| 34 bevelled section | 36 inner side bar |
| 38 outer side bar | 40 groove |
| 42 sub-groove | 44 flexible side wall |
| 46 bevelled arc | 50 iris |
| 52 cornea | 54 anterior chamber of eye |
| 56 zonules | 58 hook |
| 60 lens capsule | 62 pars plicata of ciliary body |
| 64 notch | 66 side wall opening |
| 68 attachment | 70 elastic element |
| 72 tapered profile | |

DESCRIPTION-FIGS. 1 to 22

The basic principle of the accommodating lens is illustrated in FIGS. 1 and 2. In its most rudimentary form the lens comprises a tubular rigid side wall 12 to which is attached a transparent membrane 10 on either end. Rigid side wall 12 and flexible membranes 10 together enclose a sealed lens chamber 22 which is filled with a fluid, such as a gas, with lower refractive power than the surrounding aqueous. At least one of the two membranes 10 is made to have a concave shape and at least one of the two membranes 10 is made out of a resilient material so as to allow its surface to change shape. In the most typical embodiment, as in FIGS. 1, 2, 4, 5, 10, 11, 19 and 21, both optical surfaces are concave, i.e., the lens is biconcave, and both membranes 10 are made from resilient materials. In the preferred embodiment the concave shape is created by maintaining the pressure in lens chamber 22 lower than that in the surrounding fluid. Alternatively, transparent membranes 10 may be cast so as to have a natural concave shape. Since the refractive index of the medium in the interior of the lens is less than that of the surrounding medium, the concave lens has positive power. The power of the lens can be varied by varying the curvatures of the optical surfaces, or by varying the curvature of at least one of the two optical surfaces. FIG. 1 shows the lens in a condition in which the surfaces are only moderately curved, i.e. radius of curvature is relatively long. In this state the power of the lens is moderate as is illustrated by the fact that two parallel light rays 20 are brought to a focus relatively far from the lens. In FIG. 2 the curvature is increased, i.e. the radius of curvature is decreased, and the power of the lens is increased as demonstrated by a shorter focal length.

FIG. 3 shows a transverse cross section through the lens illustrating the tubular shape of rigid side wall 12.

Figure 5:
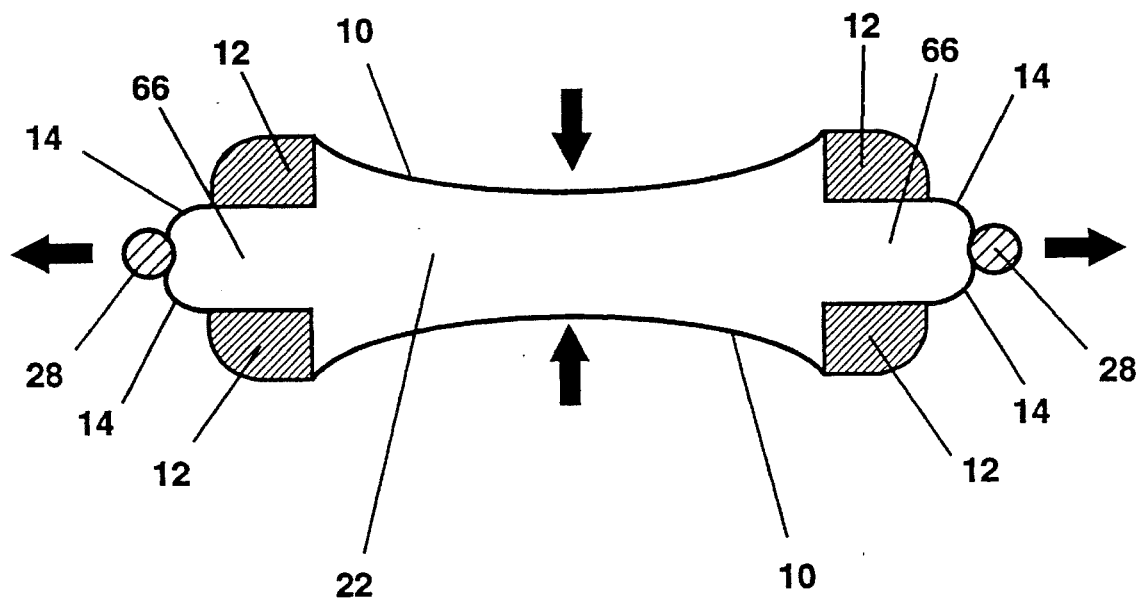
FIG. 5 shows a longitudinal cross section through the lens body to illustrate the changes in the shape of the transparent flexible membranes as the cross bars are shifted away from the optic.

In order to increase the power of the lens, at least one of the optical surfaces is made to take on a more concave shape. This can be done by decreasing the internal pressure in lens chamber 22 which will increase the pressure difference across the membranes and thereby increase the inward acting force so as to bend transparent flexible membranes 10 inward. Decreasing the internal pressure can be achieved by increasing the volume of the lens. In order to be able to do this, parts of rigid side wall 12 are removed. The resulting side wall openings 66 are covered with flexible membranes, each such membrane is referred to as flexible part of side wall 14. To flexible part of side wall 14 is attached a rigid bar, referred to as cross bar 28. Cross bar 28 is attached to flexible part of side wall 14 in such a manner as to be able to pull flexible part of side wall 14 outward. This is illustrated in FIGS. 4 and 5. As can be seen in FIG. 5, outward movement of cross bar 28 and flexible part of side wall 14 (horizontal arrows) increases the internal volume of lens chamber 22 decreasing the internal pressure with the result that transparent membranes 10 are deflected inward (vertical arrows) and made more concave.

Figure 6:
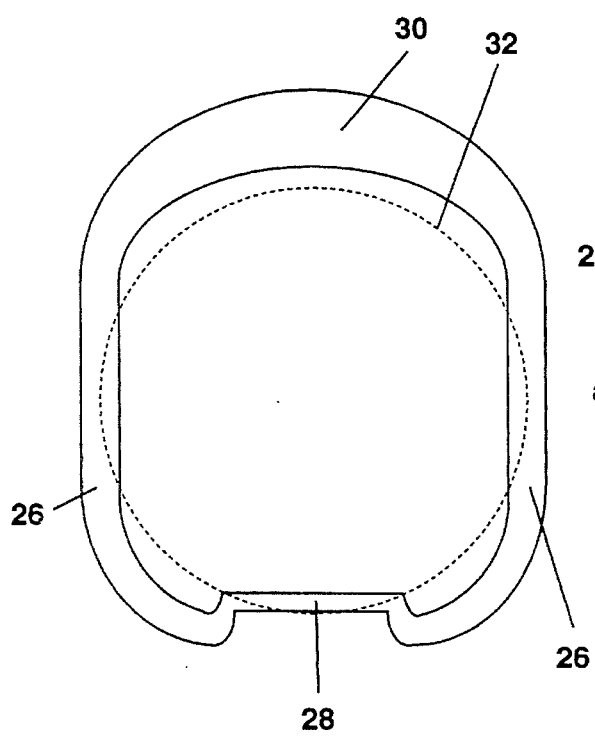
FIG. 6 shows the shape of a single haptic of a type which is made to surround the optic.

FIG. 6 shows the outline of one haptic to be used with the present lens. The haptic is made to surround the optic 32 and comprises a contact section 30 where the haptic makes physical contact with the lens capsule, a side bar 26 on either side of optic 32 and a cross bar 28. Side bars 26 serve to transmit movement in the lens capsule from contact section 30 to cross bar 28. Contact section 30 has a curvature corresponding to the curvature of the lens capsule so as to ensure that contact section 30 makes contact with the lens capsule over a considerable portion of its length. This serves to distribute the pressure on the lens capsule and prevent the lens from rotating around the long axis of the haptics.

Figure 7:
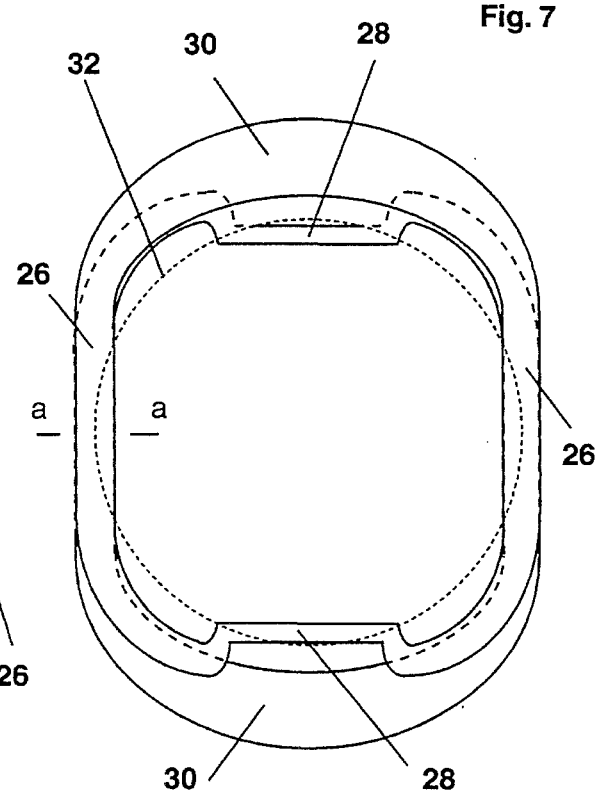
FIG. 7 shows the placement of two haptics of the type shown in FIG. 6.
Figure 8:
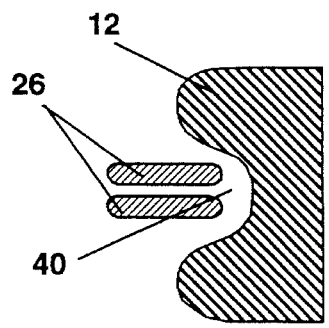
FIG. 8 shows a cross section through the side wall of the lens and through the side bar of haptics at the position indicated by a—a in FIG. 7 so as to illustrate how the side bars are made to fit in a groove in the side wall.
Figure 9:
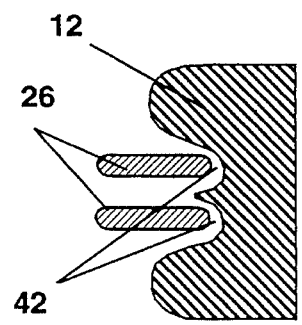
FIG. 9 shows an arrangement similar to that in FIG. 8 except that the two side bars have been provided with separate sub-grooves.

Each lens is equipped with a pair of haptics. FIG. 7 shows the arrangement of one such pair (the parts of one haptic that are obscured by the other are shown with dashed lines). The two haptics slide over each other and are held in place, relative to the plane of the optics, by grooves in rigid side wall 12 into which fit side bars 26. This is illustrated in FIGS. 8 and 9 which show cross sections through side wall 12 and side bars 26 at the place indicated by a—a in FIG. 7. In FIG. 8 is shown an arrangement in which two side bars 26 slide in a common groove 40. A variation is shown in FIG. 9 where each side bar 26 has been provided with its own sub-groove 42.

When the lens capsule contracts this increases the pressure on the haptics at contact section 30. Since the haptic is relatively rigid this in turn causes the whole haptic, including side bars 26 and cross bar 28, to move as a unit. Because contact section 30 and cross bar 28 are on opposite sides of optic 32, when contact section 30 moves inward, toward optic 32, cross bar 28 moves outward, away from optic 32. Cross bar 28 is attached to a flexible part of side wall 14 in such a manner that when it moves away from optic 32 it pulls flexible part of side wall 14 with it. This increases the volume of the lens, and since lens chamber 22 is sealed, it reduces the pressure in this chamber. The resulting pressure difference, or increase in pressure difference, across transparent membranes 10 causes these membranes to be deflected inward. This is indicated by vertical arrows in FIG. 5. Since transparent membranes 10 are attached to rigid side wall 12 along their periphery, this causes transparent membranes to take on a more concave shape. Since lens chamber 22 is filled with a medium of lower refractive index than the surrounding aqueous, this increases the positive power of the lens.

Figure 10:
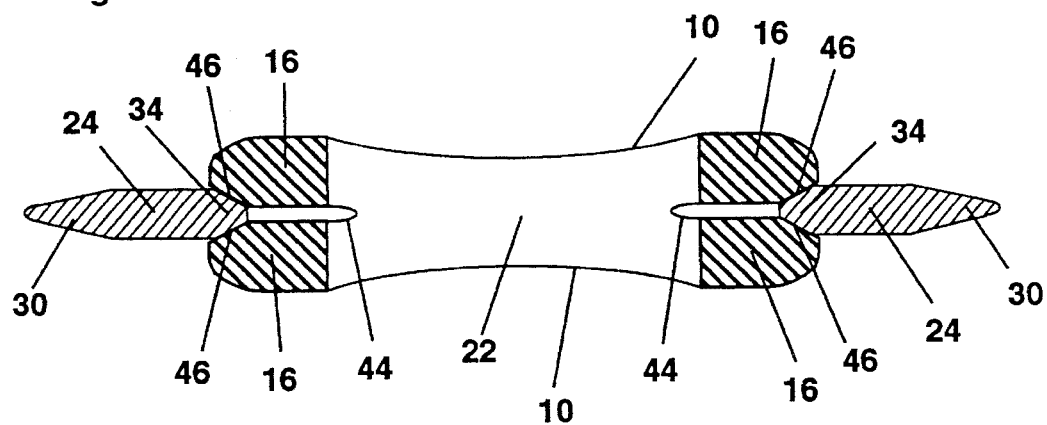
FIG. 10 shows a longitudinal cross section through a lens formed with two rigid side wall rings.
Figure 11:
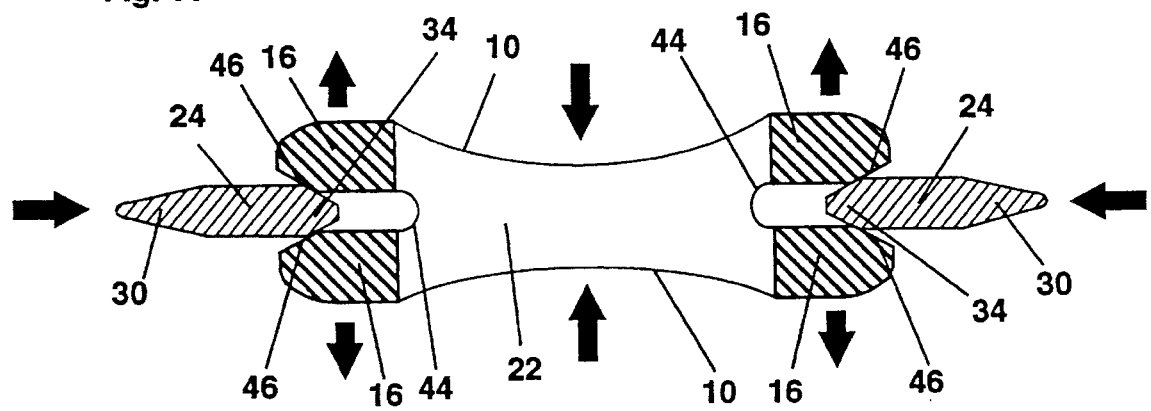
FIG. 11 shows the effect of compressing the haptics on a lens formed with two rigid side wall rings.

Decreasing the pressure in lens chamber 22 can also be achieved in another way. Instead of displacing flexible part of side wall 14 it is possible to increase the volume of lens chamber 22 by increasing the thickness of the lens. To achieve this, the single rigid side wall 12, of FIGS. 1–5, is replaced by two rigid side wall rings 16. One transparent membrane 10 is attached to each ring 16. Side wall rings 16 are parallel and joined by a flexible side wall 44. Together, the two side wall rings 16, two transparent membranes 10 and flexible side wall 44 enclose lens chamber 22 so as to form a sealed space. A lens of this type is shown in FIG. 10. In order to increase the thickness of the lens, rigid side wall rings 16 are shifted away from each other. This increases the thickness of the lens and increases the volume of lens chamber 22. Since lens chamber 22 is sealed from the surrounding medium this results in decreased pressure which in turn causes transparent membranes 10 to be displaced inward so as to be more strongly concave. This is illustrated in FIG. 11. Since the lens is filled with a medium of lower refractive index than that of the surrounding medium this causes the lens to increase its power.

In order to translate changes in lens capsule size to changes in lens thickness each haptic is equipped with a bevelled section 34. Bevelled section 34 acts as a wedge to force the two rigid side wall rings apart when the haptics are compressed as can be seen in FIG. 11. This increases the volume of lens chamber 22 which in turn decreases the pressure in this chamber so as to make transparent membranes 10 become more concave so as to increase the power of the lens. The amount of separation between the two halves of the lens depends on the amount of force exerted on the haptics. The stronger the inward force applied to the haptics, the further inward are pushed the bevelled sections 34, the larger the separation between the two rigid side wall rings 16, the more concave become transparent flexible membranes 10, and the larger becomes the power of the lens.

Figure 12:
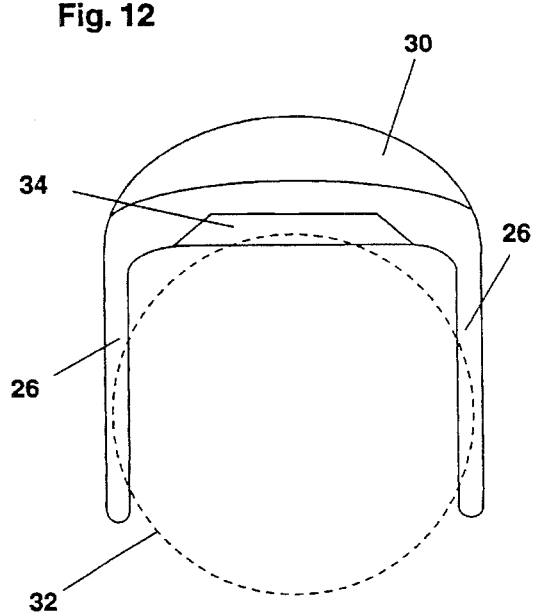
FIG. 12 shows an example of a single haptic to be used with lenses formed with two rigid side wall rings.
Figure 13:
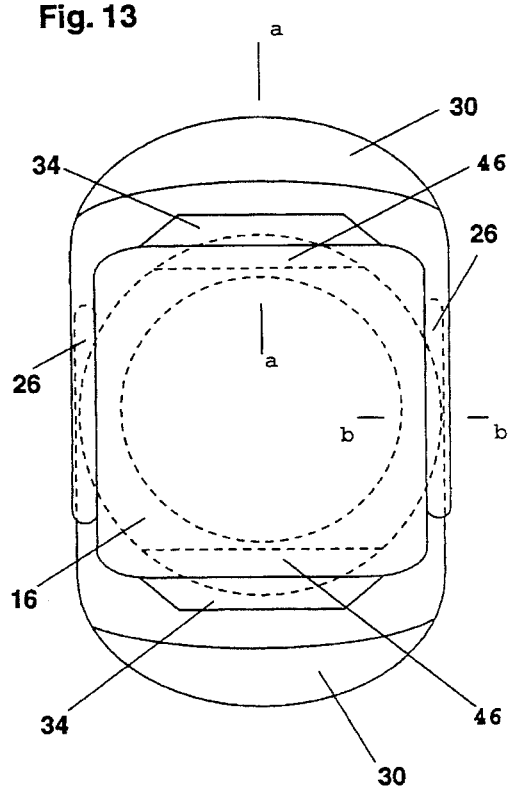
FIG. 13 shows the arrangement of a pair of haptics of the kind shown in FIG. 12.
Figure 14:
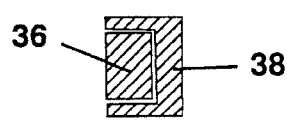
FIG. 14 shows a cross section through side bars of the haptics at the position indicated by b—b in FIG. 13.

Examples of the kinds of haptics required to vary the separation between the two halves of the lens are shown in FIGS. 12–15. FIG. 12 shows a frontal view of one sliding haptic and FIG. 13 shows a frontal view of the arrangement of a pair of sliding haptics. The haptics make contact with rigid side wall rings 16 at their bevelled sections 34. Contraction of the lens capsule causes both haptics to be pressed toward optic 32. This causes bevelled sections 34 to push the two rigid side wall rings 16 apart. Since the two halves of the lens can move relative to each other it is convenient not to have to attach the haptics to rigid side wall rings 34. In order to avoid this, side bar 26 of one haptic is made to surround side bar 26 of the other. The outer side bar 38 is given a U-shaped profile so that it may wrap around the inner side bar 36 of the other haptic. This arrangement ensures that the two haptics move in one plane. A cross section through the two side bars is shown in FIG. 14. The plane of the cross section is marked by b—b in FIG. 13. In order to prevent the optic from rotating around the long axis of the lens assembly, parts of each rigid side wall ring 16 are bevelled so as to create a pair of bevelled arcs 46. Bevelled arcs 46 of side wall rings 16 together with bevelled sections 34 of the haptic ensures that side wall ring 16 makes contact with each haptic over the length of a line or over an area and not only at a point. This prevents the optic from rotating relative to the haptic. (The outline of rigid side wall ring 16 is indicated in FIG. 13 by dashed circles.)

Figure 15:
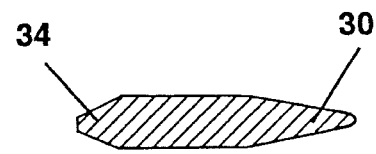
FIG. 15 shows a cross section through a haptic at the position indicated by a—a in FIG. 13.

FIG. 15 shows a cross section through the haptic at the line indicated by a—a in FIG. 13. As can be seen contact section 30 is bevelled so as to ensure that contact sections 30 fit snugly into the lens capsule equator. The outer edge of contact section 30 is rounded and smooth so as to avoid making rips in the lens capsule. Bevelled section 34 serves as a wedge as, described above, to press apart the two halves of the lens.

The relationship between the magnitude of the compression of the haptics and the amount of increase in lens power can be described as the gain of the device. The gain can be adjusted (at the time of manufacture). In the case of the embodiment in which the power is altered by deflecting part of the side wall, the gain can be varied by varying the area of flexible part of side wall 14. The larger the area the larger is the gain. That is to say, to a given compression of the haptics there corresponds a larger increase in lens power. In the case of the embodiment in which the two sides are being pushed apart, the gain is determined by the slope of bevelled section 34. The steeper the slope of the bevel the larger is the gain.

Figure 16:
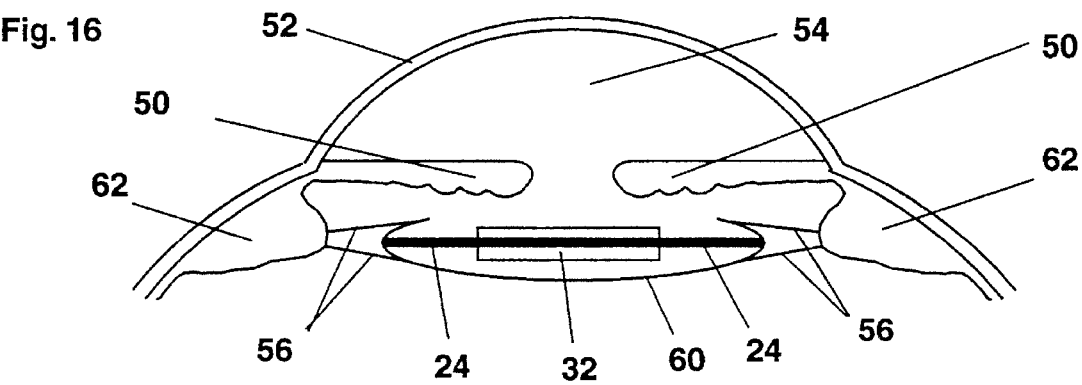
FIG. 16 shows a cross section through the anterior portion of an eye with an accommodating lens implanted in the vacated lens capsule.
Figure 17:
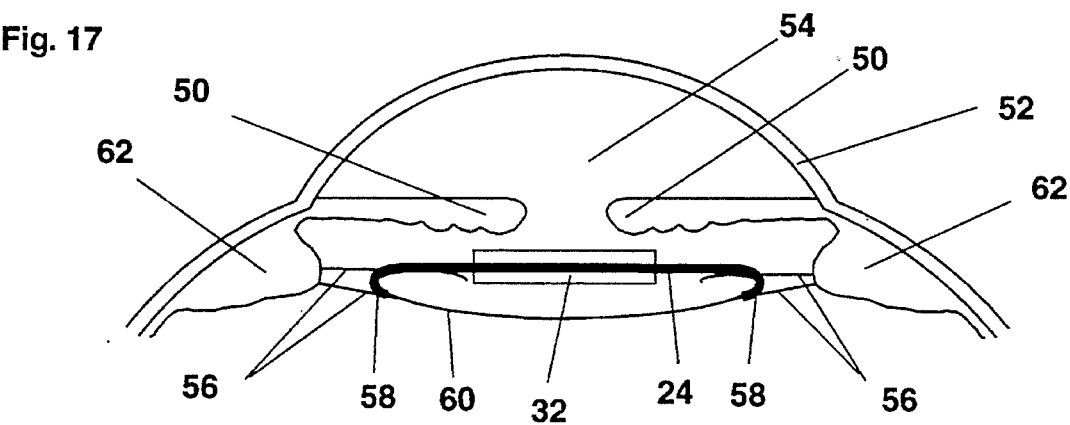
FIG. 17 shows a cross section through the anterior part of an eye in which an accommodating lens has been attached using haptics equipped with hooks that grip the edge of the empty lens capsule.
Figure 18:
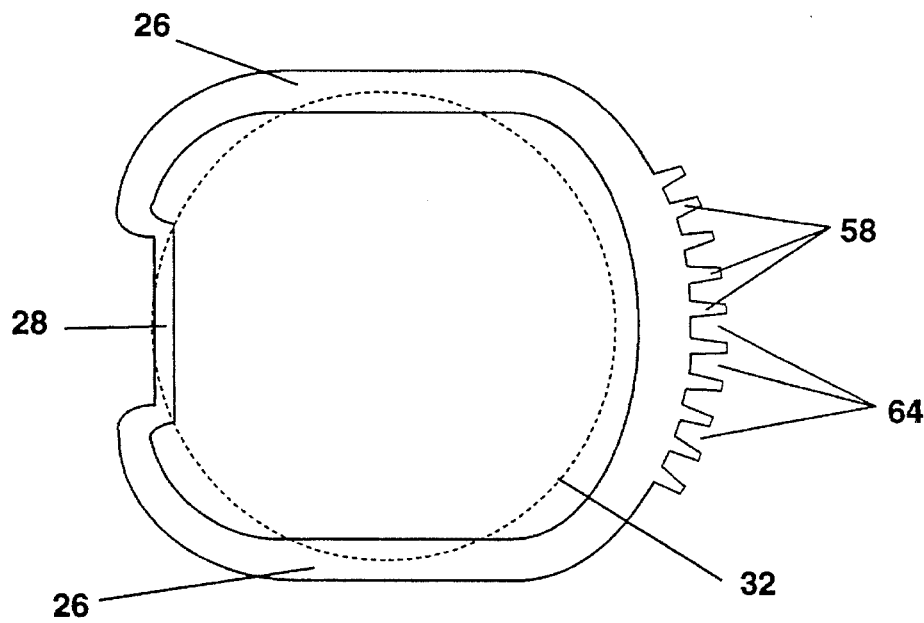
FIG. 18 shows a frontal view of a haptic equipped with a series of hooks for gripping around the outside of the lens capsule.

The above described lens is intended to be placed inside the lens capsule. Such placement is illustrated in FIG. 16. When placed inside the capsule the only force available to compress the haptics comes from the resilience of the lens capsule itself. Since it is likely that a substantial part of the anterior capsule is removed in the course of the cataract surgery, the contractive force will have to be provided mainly by the posterior capsule which may not by itself be able to provide sufficient force to actually compress the haptics, particularly as the posterior capsule is much thinner than the anterior capsule. It may therefore be necessary to be able to supply additional contractive force. In order to do so the haptics are modified so as to make it possible for them to grip around the outside of the empty lens capsule. The device is attached to the capsule with a set of hooks 58 which fit around the edge of the lens capsule. This form of placement is illustrated in FIG. 17. As can be seen, attaching the lens in this way places it somewhat anterior to the lens capsule rather than inside the capsule. FIG. 18 shows a frontal view of a haptic equipped with hooks for gripping around the edge of the empty lens capsule. As can be seen in this figure the haptic is equipped with a number of hooks 58. This is to ensure that the load on the lens capsule is well distributed. Also of significance are the notches 64 between the hooks. These are provided to allow the zonules to pass relatively freely from the lens capsule to the ciliary body without being bent or otherwise obstructed. Hooks 58 and notches 64 can be fitted both to haptics designed to deflect the side wall (i.e. lenses of the kind shown in FIGS. 6 and 7) and to haptics designed to vary lens power by changing the distance between the two halves of the lens (i.e. of the kind shown in FIGS. 12 and 13). In order to minimize damage to the delicate zonules it is important that the hooks 58 and the notches 64 between them contain no sharp edges. It may desirable to coat the haptics with a soft material, such as silicone rubber, so as to ensure that the haptics and hooks are extremely gentle on the lens capsule and the zonules. It may also be desirable to expand the haptics at the time of implantation. A tool for this purpose can easily be fashioned. With such a tool, a lens with haptics of the kind shown in FIGS. 17 through 22 can be inserted using techniques which are quite similar to those used in conventional implantation.

Figure 19:
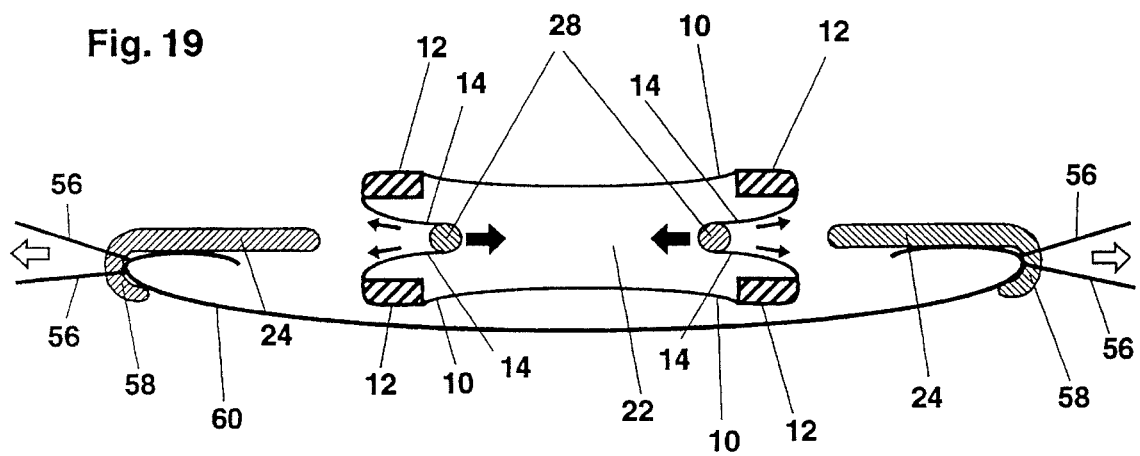
FIG. 19 shows a cross section through a lens having haptics equipped with hooks.

FIG. 19 shows the forces acting on a lens with flexible parts of side wall 14 equipped with haptics of the kind shown in FIG. 18. As can be seen, the tension in the zonules keeps the haptics extended. This is indicated by open arrows. The tension is transmitted to the haptics which pull cross bars 28 inward as is shown by the large filled horizontal arrows. This pull is opposed by the tension in the flexible parts of side wall 14 as indicated with the small solid arrows. Note that in FIG. 19 cross bar 28 on the left is connected to the haptic 24 on the right, and vice versa. When the tension in the zonules is relaxed, the tension in flexible part of side wall 14 pulls cross bar 28 outward thereby increasing the volume of lens chamber 22, which in turn decreases the internal pressure in this chamber so as to increase the power of the lens. The flexible parts of side walls 14 provide resilience and no additional elastic elements are required.

Figure 20:
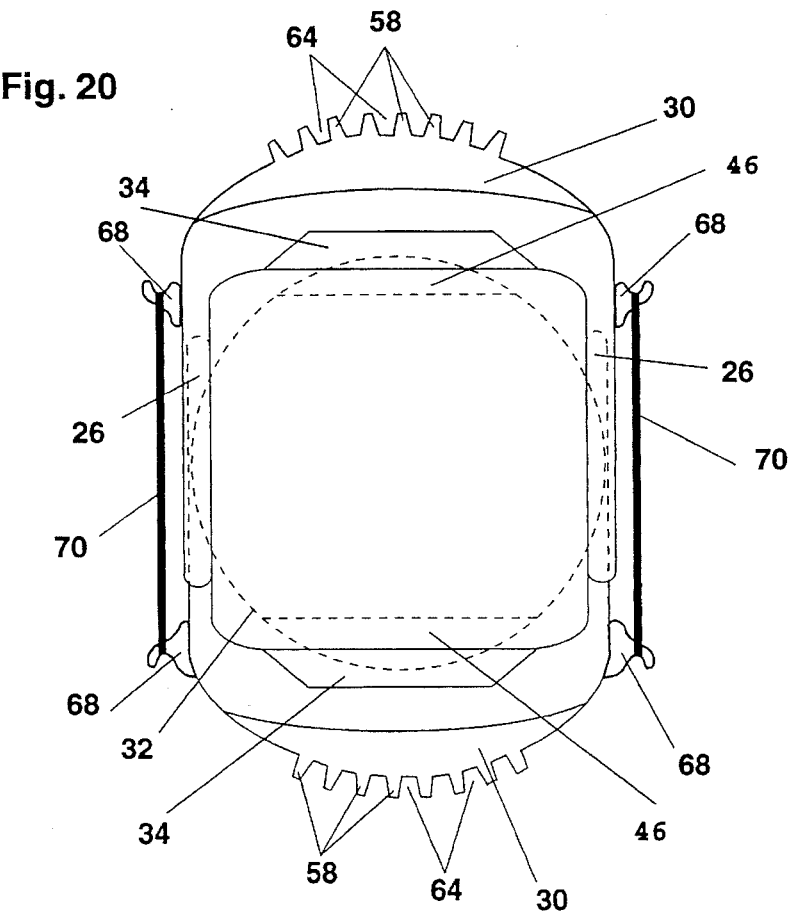
FIG. 20 shows a pair of sliding haptics equipped with hooks and elastic elements to compress the haptics.

In the case of the embodiment which alters its power by changing the distance between the two rigid side wall rings 16 additional elastic elements are required. An example of this is shown in FIG. 20 in which two elastic elements 70 have been added so as to compress the haptics. These elastic elements 70 are attached to the haptics using special attachments 68. FIG. 20 is mainly intended to illustrate the principle of how the haptics may actually be compressed by adding elastic elements. A more sophisticated solution (not shown) would be to use an elastic material, such as silicone, to coat the hooks of the haptics As described above, such a coating would make the haptics more gentle on the lens capsule and on the zonules. By making elastic elements 70 out of the same material as is used in the coating one can fuse the elastic elements and the coating. In this way no special attachments 68 are required and the elastic material will cover the whole circumference of the haptics.

Figure 21:
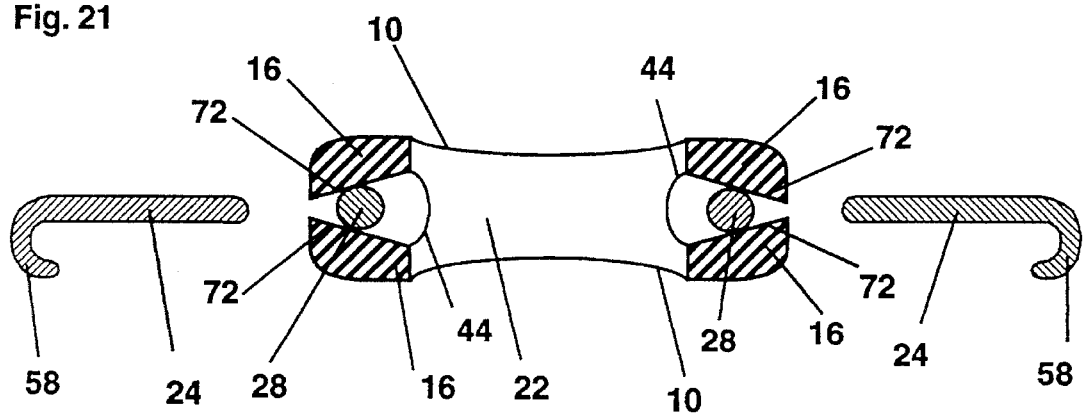
FIG. 21 shows a cross section through a lens comprising two rigid side wall rings and haptics which surround the optic.
Figure 22:
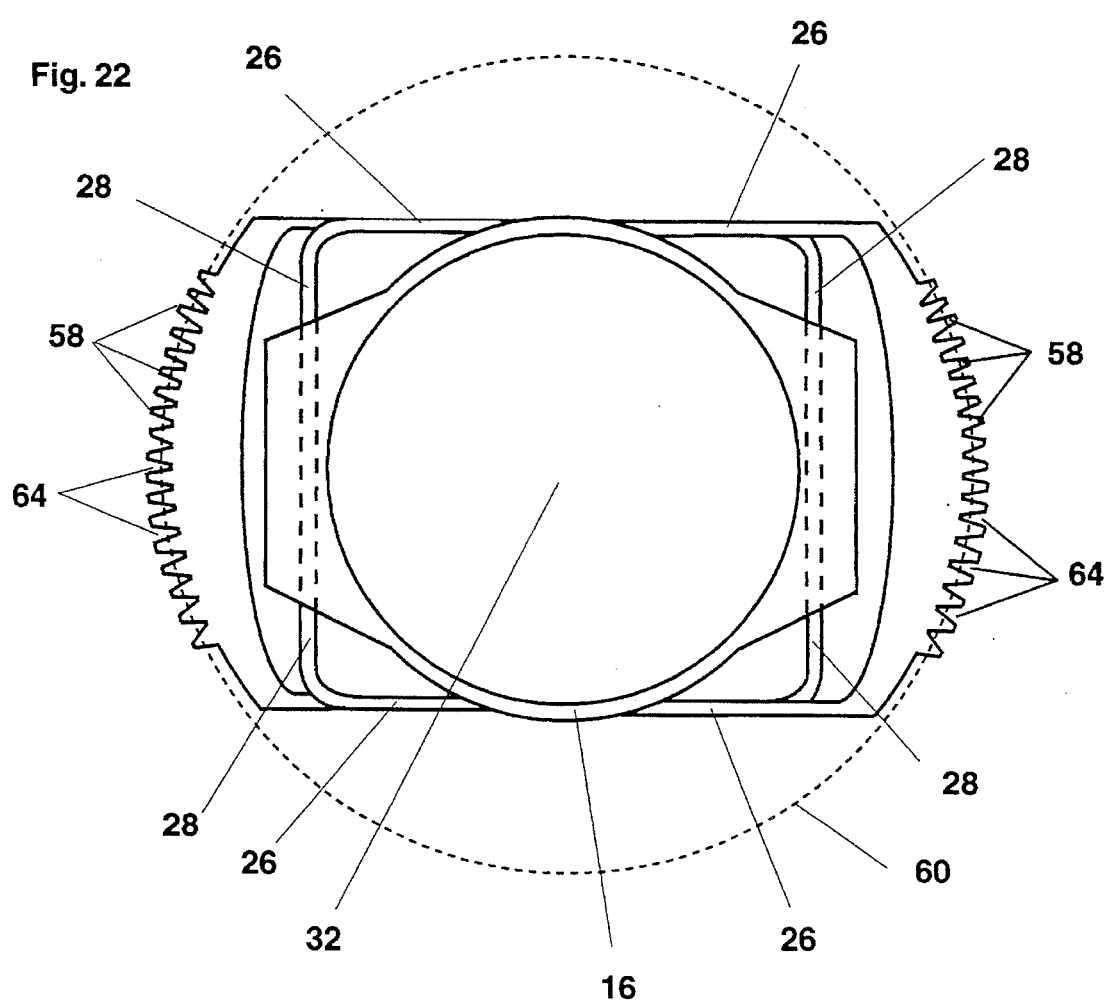
FIG. 22 shows a frontal view of the lens shown in FIG. 21.

A further variation is shown in FIGS. 21 and 22. In these figures is shown a lens made from two rigid side wall rings 16 but equipped with a pair of haptics that surround the optic. At one end the haptics are fitted with a series of hooks 58 separated by notches 64. The hooks 58 grip the lens capsule. At the other end of each haptic is a cross bar 28. The two ends of each haptic are attached to each other by a pair of rigid side bars 26. Cross bars 28 make contact with rigid side wall rings 16 at a place where these have been given a tapered profile 72. The direction of this taper is such that the two rigid side wall rings 16 are allowed to move closer when cross bars 28 move toward the center of the lens. Conversely, rigid side wall rings 16 are pushed apart when the cross bars 28 are displaced outward from the center of the lens. This increase in separation causes the volume of lens chamber 22 to increase, thereby decreasing the internal pressure in the lens so as to make the transparent membranes 10, or at least one of them, more concave; this in turn increases the power of the lens. Because the position of cross bar 28 is controlled by the tension in the zonules on the opposite side of the optic, an increase in lens power will occur when the tension in the zonules is decreased. As was the case in FIGS. 19 and 20 the lens in FIGS. 21 and 22 will have to be provided with elastic elements to compress the haptics. As was pointed out when discussing the lens of FIGS. 19 and 20, the elastic elements may be made from the same materials as the coating of the haptics, in which case no special attachments need be furnished.

Figure 23:
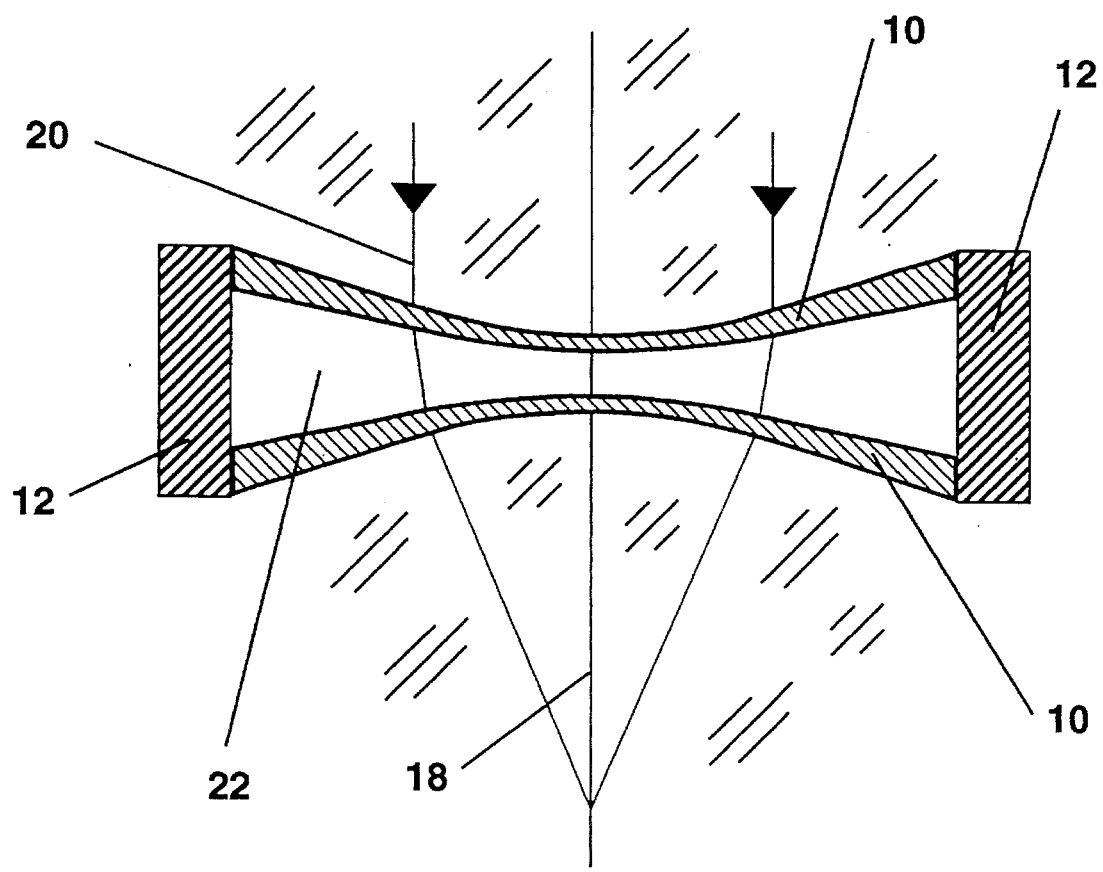
FIG. 23 shows a longitudinal cross section through the lens with membranes of uneven thickness.

FIG. 23 shows a cross section of a lens having membranes (10) of uneven thickness.

Based on the above descriptions a number of advantages of the present intraocular lens become evident:

(a) The lens has the ability to change its power in response to tension in the ciliary muscle.

(b) The lens is simple in design and has few moving parts.

(c) The lens has approximately the same outline and size as currently used intraocular lenses so that it can be inserted in the eye using standard surgical procedures.

(d) Since the lens can be filled with a gas it can be made to be lightweight.

(e) When filled with a gas there will be a large difference in refractive index between lens interior and the surrounding medium, which allows the lens to have little volume and to be able to accommodate with little change in curvature of the optical surfaces.

(f) The lens may be made quite robust so as to tolerate being handled.

(g) Both embodiments of the present invention can easily be equipped with elastic elements so as not to have to rely on the resilience of the lens capsule to compress the haptics.

OPERATION-FIGS. 1 to 22

The present lens is designed to be placed in the posterior chamber of the eye and to be compatible with either conventional extracapsular cataract extraction or lens extraction through phacoemulsification. The device is so designed as to be compatible with large anterior capsulectomies.

The principle of the lens is to enclose a fluid medium, such as a gas, with lower refractive index than the surrounding aqueous in a space between two circular transparent membranes 10 suspended along their periphery from a rigid circular structure. At least one of the two transparent membranes 10 has a concave shape which, because of the lower refractive index of the medium in the interior of the lens relative to the refractive index of the surrounding aqueous, gives the lens positive power. This concave shape can be created by making the pressure inside the lens be lower that the ambient pressure. Alternatively the membrane can be cast so as to have a concave shape at rest when no force is acting on the membrane.

The power of the lens is varied by changing the curvature of one or both of transparent membranes 10. The power of the lens is increased by making one or both of the transparent membranes 10 more concave. This increase in curvature is achieved by reducing the pressure in lens chamber 22. Thus the power of the lens can be varied by varying the pressure in the interior of the lens.

Means are provided for allowing the tension of the lens capsule to control the internal pressure in lens chamber 22. The pressure is varied by varying the volume of lens chamber 22. As is known from Boyle's Law, pressure and volume are inversely related. Thus increasing the volume reduces the pressure. Since the overall shape of the lens is similar to a cylinder there are effectively two manners in which the volume can be altered: (a) by increasing the diameter of the cylinder, or displacing a part of its side wall, or (b) by increasing the height of the cylinder, i.e., by changing the thickness of the lens. It is possible to have movement of the haptics alter the volume in either of these two ways. Two embodiments of the present inventions are therefore described.

(a) First embodiment: displacement of part of the side wall. When the ciliary muscle contracts, the tension in the zonules is released and the lens capsule, since it is resilient, is allowed to contract. In order for contraction of the capsule to translate into increased lens power the present invention makes use of haptics which surround optic 32 and are connected to cross bar 28 located on the side of optic 32 opposite to where the haptic makes contact with the lens capsule. Contact section 30 is the part of the haptic which makes physical contact with the lens capsule. Cross bar 28 and contact section 30 are connected with a pair of relatively rigid side bars 26. When the haptics are compressed, that is to say, when contact sections 30 on both haptics are displaced inward toward optic 32, cross bars 28 on both haptics move away from optic 32. Since flexible part of side wall 14 is attached to each cross bar 28, flexible part of side wall 14 is pulled outward along with cross bar 28 when the haptics are compressed. In this manner the volume of the device is increased when the haptics are compressed. Various aspects of this first embodiment of the invention are illustrated in FIGS. 4–9.

(b) Second embodiment: changing the thickness of the lens. It is possible to have constriction of the lens capsule result in an increase in lens volume by increasing the thickness of the lens, i.e. by increasing the height of the cylinder. Instead of having the lens be made with a single annular rigid side wall 12 the lens is made using two annular rigid side wall rings 16. These rings are stacked on top of each other. One transparent flexible membrane 10 is attached to each ring and the two rings are connected with flexible side wall 44. Flexible side wall 44 connects the two rigid side wall rings 16 throughout the whole circumference of optic 32 in such a manner as to allow the two rigid side wall rings 16 to move relative to each other along the optical axis of the lens while remaining parallel to each other. Together two transparent flexible membranes 10, two rigid side wall rings 16, and flexible side wall 44 form a sealed and enclosed lens chamber 22. In order to increase the volume of the lens the two rigid side wall rings 16 are pushed apart. In order for the haptics to be able to do this, the side of the haptics closest to the optic is given a bevelled shape. When the lens capsule contracts and the haptics are pushed closer to each other, bevelled sections 34 of the haptics act as wedges pushing rigid side wall rings 16 apart. This causes the volume to increase and the internal pressure to decrease. This in turn causes transparent membranes 10 to become more concave, thereby increasing the power of the lens (see FIG. 11). Once the pressure on the haptics from the lens capsule is released, rigid side wall rings 16 will again move in closer together and resume their original position. This is due to the resilience of the transparent membranes 10 which are stretched when the lens becomes more concave. Thus the lens will require no additional elastic elements in order to resume its original state. Various aspects of this second embodiment are illustrated in FIGS. 10–15.

Since the haptics are relatively rigid the overall elasticity of the lens is mainly determined by the flexibility of transparent membranes 10. As the haptics are compressed, transparent flexible membranes 10 are displaced inward by the difference in pressure across the membranes as shown in FIGS. 5 and 11. This inward movement is countered by the tension in flexible membranes 10. Equilibrium is established when the tension in the membranes balances the difference in pressure. This will transmit elasticity to the haptics so as to make them compress elastically without requiring any additional elastic parts. Thus, the resilience of transparent membranes 10 will make the haptics rebound when tension in the capsule is released.

The amount of spherical aberration and coma of a lens depend substantially on the shape factor of the lens. In order to minimize these aberrations it may be desirable to be able to manipulate the shape factor. To do so one needs to manipulate the relative curvature of the two optical surfaces. This can be done by making the two transparent membranes 10 have somewhat different thickness or stiffness, in which case one flexible membrane 10 can be made more curved than the other. Since both transparent membranes 10 may be made from flexible materials it is possible to select the relative thickness or stiffness of the two membranes 10 such that as the power is changed the shape factor of the lens remains relatively invariant. Thus it is possible to have the lens maintain a shape factor so as to minimize, or approximately minimize, the effects of spherical aberration and coma over the full range of lens powers.

Because the device is essentially hollow it can be made so as to be of very light weight and to have little mass. This is an advantage during saccades when the eye accelerates and decelerates rapidly, at which time a lens with a smaller mass puts less load on the structures in the eye which are in contact with the lens.

In order to prevent the flexible elements of the lens from being overstretched it may be desirable to introduce stopping devices to restrict the travel of the haptics. In the case of the design with two rigid side wall rings 16 it may be desirable to directly restrict the amount of possible separation between rigid side wall rings 16.

The zonules pull the lens capsule outward. This pull is balanced only by the resilience of the lens capsule. In the case of an intraocular lens placed in the lens capsule, as shown in FIG. 16, the only inward pressure acting on this lens is therefore provided by the resilience of the lens capsule. It may be that the capsule, or what remains of it after the cataract has been removed, does not provide sufficient force to compress the haptics. In which case it will be necessary to provide the lens with its own inward acting force. This can be done with a relatively minor modification of the haptics. A series of hooks are attached at the outward edge of the haptics. These hooks fit around the periphery of the lens capsule, as shown in FIG. 17. The haptics are maintained in a somewhat extended state by the outward pull provided by the zonules. This pull is counterbalanced by an inward pull provided by the resilience of the lens and haptics (and lens capsule). When the ciliary body contracts the tension in the zonules is relieved and the inward pull provided by the lens becomes larger than the outward pull provided by the zonules. The haptics will contract until a new equilibrium is established. As a result of this contraction the lens increases its power, that is to say, it accommodates.

This arrangement places the lens somewhat anterior to, rather than inside, the capsule. An advantage of having the lens be placed outside the lens capsule is that there is less danger that parts of the capsule may interfere with the operation of the lens. A further advantage of having the lens provide its own inward pull and not having to be reliant on the resilience of the lens capsule, is that laser capsulotomy of the posterior capsule can be performed with minimal effect on the operation of the lens. Placing the lens anterior to the capsule facilitate such laser treatment as it provides spatial separation between lens and capsule.

SUMMARY, RAMIFICATIONS, AND SCOPE

The reader will see that this invention of an accommodating intraocular lens can be made to alter its power in response to the tension in the ciliary muscle. The lens has the following advantages in that:

- it is simple in design making it relatively easy to manufacture.
- it can be filled with air which is relatively easy to sterilize by filtering and which is non-toxic to the intraocular environment.
- it can be manufactured so as to be very light and have little mass.
- it has few moving parts.
- it can be manufactured so as to have no sharp edges which can irritate the delicate tissue in the eye.
- it is compatible with standard extracapsular lens extraction or phacoemulsification surgery.
- it is robust in design and its various optical elements can not easily be misaligned as a result of handling.
- it is compatible with capsulectomy of an extensive portion of the anterior capsule.
- it can easily be modified so as not to be dependent on the resilience of the lens capsule.

Although the description above contains many specificities, these should not be construed as limiting the scope of the invention but as merely providing illustrations of some of the presently preferred embodiments of this invention. For example the exact shapes of the haptics may be different from the ones shown in the figures. Also, in the descriptions above both transparent membranes were made from resilient materials; in order for the present lens to work only one of these membranes needs to be resilient. Thus the scope of the invention should be determined by the appended claims and their legal equivalents, rather than by the examples given.

I claim:

1. A lens for implantation in the human eye, said lens is so constructed so as to be thinner at its center than at its periphery said lens comprising two refractive surfaces, at least one of the two refractive surfaces of said lens has a concave shape and at least one of said refractive surfaces is formed by a membrane made from a resilient material allowing said at least surface to alter its shape in response to changes in tension in the ciliary muscle, contained between said surfaces is a fluid medium of refractive index smaller that of aqueous of the eye thereby giving the lens a variable amount of positive power.

2. A lens such as described in claim 1, further comprising for the tension in the ciliary muscle of the eye to alter the shape of at least one of the refractive surfaces in such a way that higher tension in the ciliary muscle makes at least one of said refractive surfaces be more concave thereby increasing the positive power of said lens.

3. A lens as described in claim 1 further comprising haptics to fit in a lens capsule of the eye after the natural lens has been extracted as part of cataract surgery, said haptics are connected in such a manner that compression of said haptics causes reduced pressure in the interior of said lens so as to make at least one of said refractive surfaces of said lens be more concave thereby increasing the positive power of said lens.

4. A lens as described in claim 1 further comprising a sidewall extending between said two refractive surfaces and haptics to fit in a lens capsule as of the eye after the natural lens has been extracted as part of cataract surgery, said haptics are connected in such a manner that compression of said haptics causes sections of the side wall of said lens to be deflected outward thereby reducing pressure in the inside of said lens in such a manner as to make at least one of said refractive surfaces of said lens be more concave thereby increasing the positive power of said lens.

5. A lens as described in claim 1 further comprising haptics to fit in a lens capsule of the eye after the natural lens has been extracted as part of cataract surgery, said haptics are connected in such a manner that compression of said haptics causes the distance separating the two refractive surfaces of said lens to increase, thereby increasing the volume of said lens which in turn reduces the pressure in the inside of said lens, thereby increasing the concave shape of at least one of said refractive surfaces in such a manner as to increase the positive power of said lens.

6. A lens as described in claim 1 further comprising a sidewall extending between said two refractive surfaces and haptics having hooks so as to grip around outer edges of a lens capsule of the eye after the natural lens has been extracted as part of cataract surgery, said haptics are connected in such a manner that reduced tension in the zonules causes sections of the side wall of said lens to be deflected outward thereby reducing pressure in the interior of said lens in such a manner as to make at least one of said refractive surfaces be more concave thereby increasing the positive power of said lens.

7. A lens as described in claim 1 further comprising haptics having hooks so as to grip around outer edges of a lens capsule of the eye after the natural lens has been extracted as part of cataract surgery, said haptics are connected in such a manner that decreased tension in the zonules causes the distance separating the two refractive surfaces of said lens to increase, thereby increasing the volume of said lens which in turn reduces the pressure in the interior of said lens, thereby increasing the concave shape of at least one of said refractive surfaces in such a manner as to increase the positive power of said lens.

8. A lens as described in claim 1 in which both of said refractive surfaces are resilient.

9. A lens as described in claim 1 in which both of said refractive surfaces consist of transparent flexible membranes, the membranes having a thickness relative to one another which causes the relative curvature of said membranes to obtain a shape factor that will minimize aberrations.

10. A lens as described in claim 1 in which both of said refractive surfaces are transparent flexible membranes, the membranes having a rigidity relative to one another which causes the relative curvature of said membranes to obtain a shape factor that will minimize aberrations.

11. A lens as described in claim 1 in which both of said refractive surfaces are transparent flexible membranes, the membranes having a rigidity relative to one another that creates a shape factor appropriate for obtaining minimal aberrations, said shape factor being maintained over a range of lens powers.

12. A lens as described in claim 1 in which said fluid medium filling said lens is a gas.

13. A lens as described in claim 1 with haptics equipped with hooks which fit around a lens capsule of the eye.

14. A lens as described in claim 1 in which said at least one membrane is of uneven thickness in such a manner that the thickness makes the surfaces take on aspherical profiles so as to overcome aberrations.

15. A biconcave lens for implantation in the human eye, said lens having two refractive surfaces being filled with a material with refractive index smaller than that of aqueous of the eye thereby giving said lens positive power, said lens being equipped with means whereby changes in tension of the ciliary muscle can alter the shape of at least one of the refracting surfaces of said lens.

* * * * *